United States Patent [19]

Davison et al.

[11] Patent Number: 5,877,204
[45] Date of Patent: Mar. 2, 1999

[54] COMPOUNDS CONTAINING A MICHAEL-ACCEPTOR, ESPECIALLY MALEIMIDE OR MALEIC ACID DERIVATIVES, DIRECTLY OR INDIRECTLY LINKED TO A CHROMOPHORE AND THEIR USE IN LONG LASTING SUNSCREEN COMPOSITIONS

[75] Inventors: Bruce Everett Davison, London; Bryan Colin Nicholas Morgan Jones, Dyfed; Charon Robin Ganellin, Hertfordshire; Paul Beaumont Bishop, London; David Jack, Hertfordshire, all of Great Britain

[73] Assignee: Vanguard Medica Limited, Surrey, Great Britain

[21] Appl. No.: 755,757

[22] Filed: Nov. 5, 1996

Related U.S. Application Data

[63] Continuation of PCT/GB95/01035, May 9, 1995.

[30] Foreign Application Priority Data

May 6, 1994 [GB] United Kingdom .................... 9408994

[51] Int. Cl.$^6$ ........................ A61K 31/40; C07D 201/448
[52] U.S. Cl. ............................ 514/425; 514/563; 548/545
[58] Field of Search ...................................... 514/425, 563

[56] References Cited

U.S. PATENT DOCUMENTS 3,751,449   8/1973   Gobran et al. .......................... 260/486

*Primary Examiner*—Johann Richter
*Assistant Examiner*—Laura R. C. Lutz
*Attorney, Agent, or Firm*—Gilberto M. Villacorta Pepper Hamilton LLP

[57] ABSTRACT

The present invention relates to compounds which are useful as sunscreens. The compounds persist on the skin for much longer than conventional sunscreens because they comprise a Michael acceptor linked directly or indirectly to a chromophore. The Michael acceptor is capable of undergoing a conjugate addition reaction with thiol groups present in cysteine residues of keratin and thus the compound is chemically bound to the skin and will not be removed by immersion in water.

5 Claims, 1 Drawing Sheet

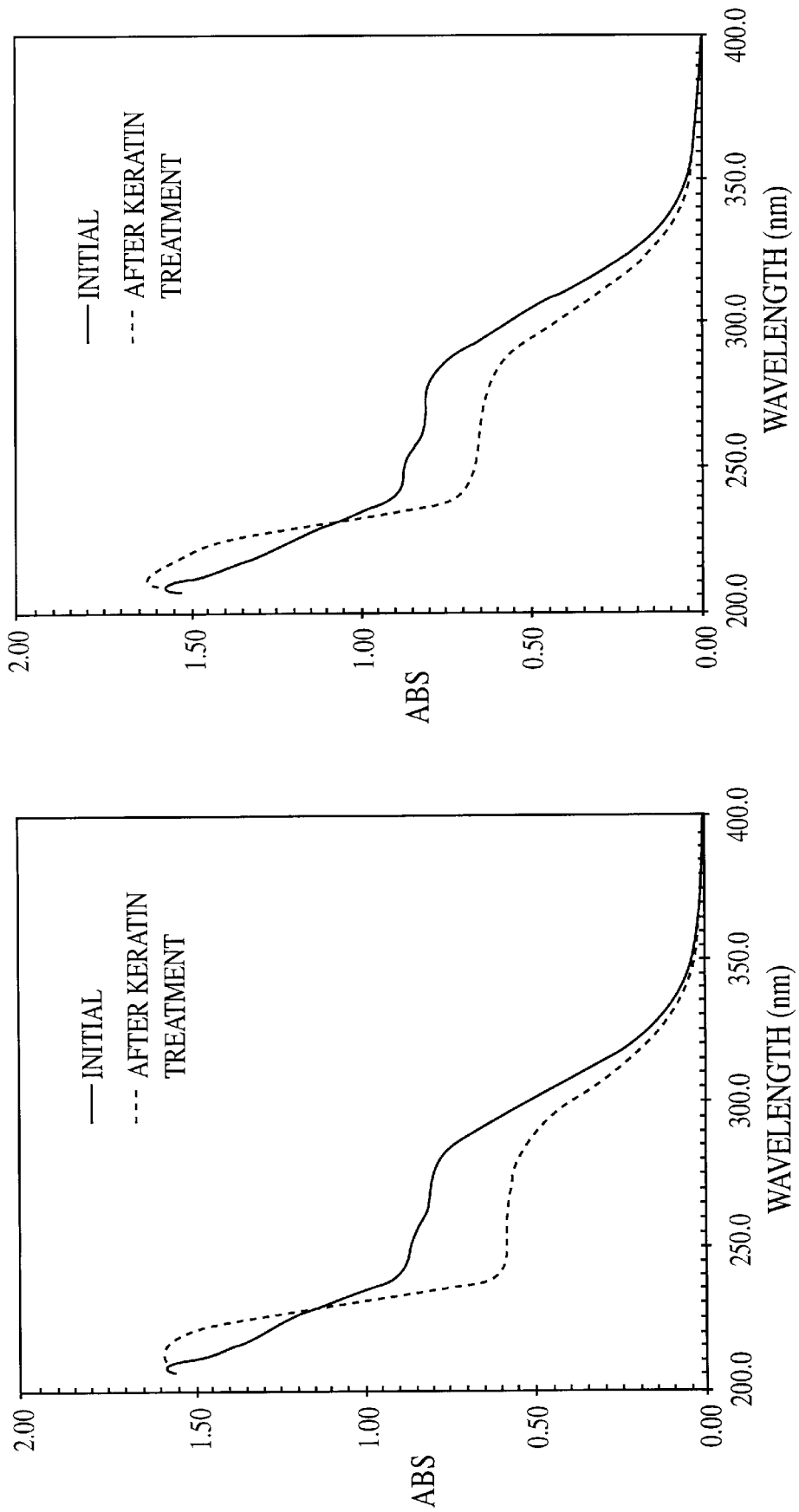

COMPOUNDS CONTAINING A MICHAEL-ACCEPTOR, ESPECIALLY MALEIMIDE OR MALEIC ACID DERIVATIVES, DIRECTLY OR INDIRECTLY LINKED TO A CHROMOPHORE AND THEIR USE IN LONG LASTING SUNSCREEN COMPOSITIONS

REFERENCE TO RELATED APPLICATION

This Application is a continuation of International Application No. PCT/GB95/01035, whose international filing date is May 9, 1995, which in turn claims the benefit of U.K. Application No. GB9408994.3, filed May 6, 1994, the disclosures of which Applications are incorporated by reference herein. The benefit of the filing and priority dates of the International and U.K. Applications is respectfully requested.

BACKGROUND OF THE INVENTION

The present invention relates to novel compounds which are useful as sunscreens and to water resistant and long lasting sunscreen compositions.

Mammalian skin comprises two main layers; the outer cellular layer is termed the epidermis and the inner layer, which is mainly non-cellular is known as the dermis. The dermis contains structural proteins such as collagen and elastin. The outer layer of the epidermis is a non-living keratin layer known as the stratum corneum and is derived from keratinocytes of which the epidermis is mainly composed. The other types of cell in the epidermis are melanocytes which synthesise melanin and Langerhans cells which present antigens to the systemic immune system.

Solar ultra violet radiation (UVR) ranges in wavelength from about 290 nm to 400 nm. Radiation of 280 to 320 nm is known as UVB and radiation of 320 to 400 nm is termed UVA. Light of wavelength 100 to 280 nm is known as UVC.

Solar UVR is known to have various photobiological effects on the skin and these include acute effects such as erythema (sunburn) and tanning as well as longer term effects such as skin cancer and premature aging. The precise mechanisms of the reactions of sunlight on the skin are not fully understood but it seems clear that the initial event is likely to be a photochemical reaction in which a chromophore present in the skin is modified after absorption of UVR. Known chromophores in the skin include urocanic acid, which is a deamination product of histidine and is present in large quantities in the stratum corneum, nucleic acids, aromatic amino acids and melanins which are complex pigments produced by the melanocytes.

Because of the well known damaging effects of sunlight on the skin, sunscreens have been in use for many years. Sunscreens are classified by their sun protection factor against simulated solar radiation which is defined by the following equation:

$$SPF = \frac{[MED_{24h} \text{ with sunscreen at 2 } \mu l/cm^2]}{[MED_{24h} \text{ without sunscreen}]}$$

Until recently, most of the adverse effects of sunlight on the skin as well as tanning have been attributed to the effects of UVB but there is now an increasing body of evidence which suggests that UVA is likely to be responsible for some of the aging and carcinogenic effects of sunlight. In particular, it has been suggested that UVA could be a cause of malignant melanoma in humans (Setlow et al, *Proc. Natl. Acad. Sci.* 90, 6666–6670). For this reason, until relatively recently most of the sunscreens were designed only to protect from UVB and offered little or no protection from UVA. Clearly, this can be dangerous to the wearer of the sunscreen since protection from erythema caused by UVB encourages longer exposure to the sun and consequently to UVA from which the wearer of the sunscreen is not protected. It is therefore widely accepted that it is desirable for sunscreen formulations to offer protection from both UVA and UVB.

There are two conventional modes of action of sunscreens. The first of these is to prevent UVR from reaching the skin which can be done by covering the skin with a pigment which will scatter UVR. Pigments which are used in sunscreens include inorganic substances such as titanium dioxide and zinc oxide and some sunscreens also include melanin. The other strategy for providing a sunscreen is to cover the skin with a substance possessing a chromophore which absorbs light of the appropriate wavelength. Substances with suitable chromophores include anthranilates, benzophenones, camphor derivatives, cinnamates, dibenzoylmethanes, p-aminobenzoic acid (PABA) and its derivatives and salicylates. Broad spectrum protection from UVR can be achieved by combining UVA and UVB absorbing substances such as 2-ethylhexyl-4'-methoxycinnamate ($\lambda$max=308 nm) and 4-$^t$butyl-4'-methoxydibenzoylmethane ($\lambda$max=355 nm).

There are, however, several problems with conventional sunscreens and one of the most serious is that they generally remain on the skin for only for a relatively short period of time. This can be dangerous as many users do not realise that their sunscreen will protect them for perhaps as little as 30 to 60 minutes when the sunlight is very intense. The problem is particularly acute for swimmers and other participants in water sports since many of the most effective sunscreens are highly soluble in water and, as water is ineffective at filtering out UVR, the user may be completely unprotected soon after entering the water. Water resistant sunscreens are available but the water resistance often arises from the way in which the compounds are formulated although water resistant sunscreens comprising a UV absorbing component attached to a polymeric backbone have also been proposed. Even with these so called water resistant sunscreens, however, it is still necessary for the user to reapply them frequently and this can be inconvenient in many water sports situations.

One approach to providing long lasting protection from UVR has been the so called "active sunscreen" formulation which includes low concentrations of the photosensitiser 5-methoxypsoralen (5-MOP) which is capable of inducing a tan which provides superior and persistent photoprotection against DNA damage. However, the use of 5-MOP has proved controversial as it photobinds to DNA and has been shown to be a photomutagen and a photocarcinogen.

SUMMARY OF THE INVENTION

There is thus a need for a sunscreen which is capable of providing long lasting protection to the user even in the water. The present invention solves this problem by providing a completely new approach to the production of sunscreens. It is intended that the sunscreen compounds of the invention, instead of merely forming a protective layer on top of the skin, will be capable of interacting chemically with the epidermis and will thus be much more persistent than the creams and lotions which form the state of the art. The keratinised cells of the stratum corneum are continually shed by the process of desquamation and the stratum corneum renews itself approximately every four days and therefore a sunscreen which is chemically attached to it would be likely to persist for about that time.

BRIEF DESCRIPTION OF THE DRAWINGS

The invention may be better understood if reference is made to the accompanying drawings.

FIG. 1. A plot showing the change in the absorption spectrum of hair keratin after reaction with N-phenylmaleimide.

FIG. 2. A plot showing the change in the absorption spectrum of horn-hoof keratin after reaction with N-phenylmaleimide.

DETAILED DESCRIPTION OF THE INVENTION

JP-A-59-204171 discloses maleimide derivatives for use as reagents for determining SH-containing compounds.

EP-A-0407932 discloses compounds for use as sunscreens which are polymers of methacrylates carrying chromophores such as hydroxylated benzophenones.

In a first aspect of the present invention, therefore, there is provided a compound for use as a sunscreen and comprising a UV chromophore attached to a group which is capable of chemical binding to mammalian skin.

Although the intention of the present inventors is to design a sunscreen which is chemically attached to the skin, it is important that it is not sufficiently absorbed for it to interact with the living cell layers of the epidermis. For this reason, it is greatly preferred that the compounds of the present invention are designed to react with the keratin of which cells of the stratum corneum are mainly composed. It is also greatly preferred that reaction of the sunscreen agent with the keratin should be relatively rapid so that penetration of unreacted compound into the skin is minimal.

The components of keratin are proteins which have a relatively high ratio of cysteine to other amino acids. Although the keratin present in the epidermis contains somewhat lower quantities of cysteine than the keratin of the hair and nails, there are still sufficient cysteine residues, and thus thiol groups, for them to be used as a point of attachment of a UVR absorbing substance.

Thiols are able to react with α,β-unsaturated carbonyl compounds or similar agents in conjugate addition reactions and this route of attachment to the skin has been found to be particularly useful.

Therefore, in a second aspect of the present invention, there is provided a compound for use as a sunscreen and comprising a UV chromophore attached directly or indirectly to a Michael acceptor.

In the context of the present invention the phrase "attached directly or indirectly" means that the UV chromophore can be either directly linked to the Michael acceptor via some part of the chromophoric entity. Alternatively, there may be indirect attachment whereby the chromophore is attached to a linker such as an alkyl or alkenyl chain which is in turn linked to the Michael acceptor.

In the context of the present invention, the term "Michael acceptor" refers to any α,β-unsaturated compound which is capable of reacting with a nucleophile in a conjugate addition reaction such as the so called Michael addition. Strictly speaking, the term Michael addition refers to a particular conjugate addition reaction in which a carbanion is reacted with an α,β-unsaturated compound whereas the present invention is primarily concerned with the situation when the nucleophile is a thiol group. However, the same groups which would undergo the Michael reaction will also react with thiols and therefore they have been termed "Michael acceptors" throughout the present specification.

Examples of Michael acceptors are well known and any compound of this type is suitable for use in the present invention. Michael acceptors include α,β-unsaturated esters, amides, carboxylic acids, nitriles, aldehydes and ketones. Specific examples include derivatives of quinone:

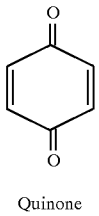

Quinone maleic and acrylic acids, and their esters and other derivatives:

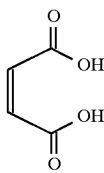

maleic acid

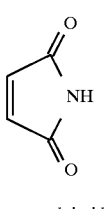

maleimide

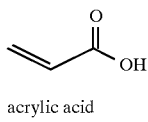

acrylic acid and other electron deficient alkenes such as acrylonitrile:

acrylonitrile

It has been found that maleic acid, maleamic acid and maleimide and their derivatives are particularly suitable for use as the Michael acceptor since they react gently yet quickly with thiol groups and thus would be unlikely to cause unpleasant side effects when applied to the skin.

The reaction of a maleimide derivative with the ethyl ester of cysteine can be represented by the following equation:

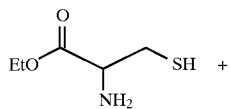

-continued

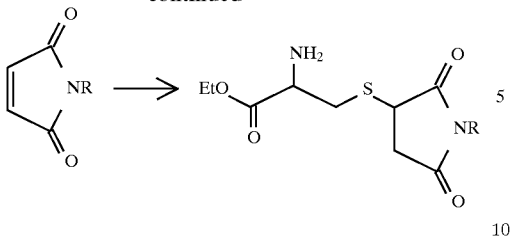

Other Michael acceptors react with the thiol group of cysteine in an analogous manner.

The Michael acceptors mentioned specifically above are well known to those skilled in the art and are either commercially available or can be prepared by methods known to those skilled in the art.

A further advantage of attaching the chromophoric group to a Michael acceptor is that the Michael acceptors are able to bind not only to free thiol groups on cysteine residues but also to other nucleophiles which are likely to be present in the skin. For example, they can react with α-amino groups which are present at the N-terminus of proteins and peptides and on the side chain of the amino acid lysine to form covalently linked succinimide derivatives. It has also been suggested that the imidazole group of histidine will react with maleimides. The UV chromophore may be selected from any one of a number of well known chromophores. It will of course be chosen so that the λmax is within either the UVA or the UVB wavelength range according to the particular type of protection which is desired.

Examples include derivatives of cinnamic acid and benzylidene which are UVB absorbers and various substituted benzophenone and dibenzoylmethane derivatives which are UVA absorbers.

The present invention relates in a third aspect to novel compounds of general formula I:

X—R                                         (I)

wherein
X is a Michael acceptor;
R is Z, $C_1-C_8$ alkyl-YZ, $C_2-C_8$ alkenyl-YZ or $C_2-C_8$ alkynyl-YZ;
Y is O, $NR^4$, $S(O)_n$, C=O or $CH_2$ and n is an integer from 0 to 2;
wherein
$R^4$ is H, $C_1-C_8$ alkyl or $C_2-C_8$ alkenyl; and
Z is a chromophore group;
with the proviso that when X represents:

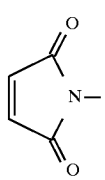

then Z is not

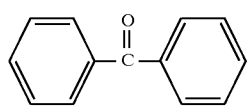

Preferably, X represents one of the following groups:

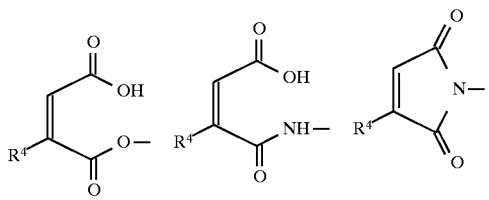

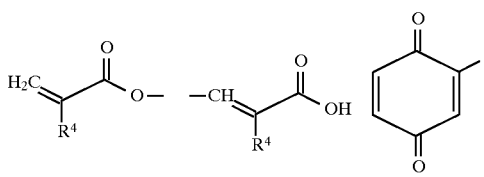

wherein
$R^4$ is H, $C_1-C_8$ alkyl or $C_2-C_8$ alkenyl; and
Z is preferably a chromophore group:

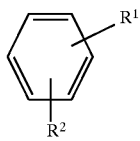

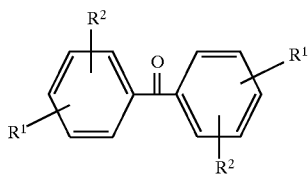

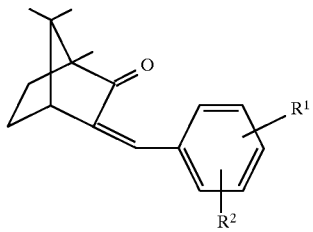

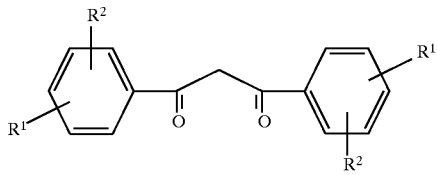

wherein
$R^1$ and $R^2$ may be the same or different and represent:
—H, —$OR^5$, —$NR^5R^6$, —$SO_3H$, chloro, fluoro, bromo, iodo, $C_1-C_8$ alkyl, $C_2-C_8$ alkenyl, $C_2-C_8$ alkynyl, phenyl, —$C_1-C_8$ alkylphenyl, —$C_2-C_8$ alkenylphenyl, —$C_2-C_8$ alkynylphenyl, —$COOR^3$, —$COR^3$, —$C_1-C_8$ alkyl$COR^3$, —$C_2-C_8$ alkenyl$COR^3$, —$C_2-C_8$ alkynyl$COR^3$, —$C_1-C_8$ alkyl$COOR^3$, —$C_2-C_8$ alkenyl$COOR^3$ or —$C_2-C_8$ alkynyl-$COOR^3$;
alternatively, either or both of $R^1$ and $R^2$ may be replaced by a group $C_1-C_8$ alkyl-YZ, $C_2-C_8$ alkenyl-YZ or $C_2-C_8$ alkynyl-YZ wherein Y and Z are as defined above;
$R^3$ is H, $C_1-C_8$ alkyl, $C_2-C_8$ alkenyl, phenyl, $C_4-C_{12}$ cycloalkyl, $C_4-C_{12}$ cycloalkenyl, $C_4-C_{10}$ cycloalkenone or $C_4-C_{12}$ cycloalkenone;
$R^5$ and $R^6$ may be the same or different and represent H or $C_1-C_8$ alkyl.

It can be seen that all of the above compounds conform to the general pattern of a Michael acceptor linked to a chromophore or to a pair of unconjugated chromophores.

In the present invention the term "$C_1$–$C_8$ alkyl" refers to a straight or branched chain alkyl group having from one to eight carbon atoms. Examples of such groups include methyl, ethyl, n-butyl, t-butyl and n-hexyl.

In the present invention, the term "$C_2$–$C_8$ alkenyl" refers to a straight or branched chain alkenyl group having from two to eight carbon atoms. Examples of such groups include ethenyl, propenyl, 1-butenyl and 2-butenyl.

In the present invention, the terms "$C_4$–$C_{12}$ cycloalkyl" and "$C_4$–$C_{12}$ cycloalkenyl" refer respectively to substituted or unsubstituted cyclic alkyl and alkenyl groups having from 4 to 12 carbon atoms. Such groups include cyclobutyl, cyclohexyl, cyclohexenyl and more complex ring systems such as norbornyl and norbornylene.

It is preferred that the group X represents either a maleimido group or a maleamic acid residue since compounds based on these Michael acceptors are particularly easy to synthesise and react readily yet mildly with thiols.

It has been found that good results are obtained when the group R is a substituted phenyl group, a benzophenone or substituted benzophenone or a cinnamic acid derivative.

The following compounds of general formula I are particularly useful:
N-(4-carboxyphenyl)maleamic acid;
N-(4-carboxyphenyl)maleimide;
N-(4-benzoylphenyl)maleamic acid;
N-(4-benzoylphenyl)maleimide;
N-[4-(2-carboxy-(E)-ethenyl)phenyl]maleamic acid;
N-[4-(2-carboxy-(E)-ethenyl)phenyl]maleimide;
N-[4-(2-carboxy-(Z)-ethenyl)phenyl]maleamic acid;
N-[4-(2-carboxy-(Z)-ethenyl)phenyl]maleimide;
N-(4-methoxycarbonylphenyl)maleamic acid;
N-(4-methoxycarbonylphenyl)maleimide;
N-(4-n-butyloxycarbonylphenyl)maleamic acid; and
N-(4-n-butyloxycarbonylphenyl)maleimide.

It has been found that the UV characteristics of the chromophores used in the compounds of the invention are changed somewhat on directly attaching a Michael acceptor and subsequently reacting the product with a thiol. Generally, it has been found that the λmax of the chromophore falls slightly on attaching the Michael receptor with a rather larger fall on reaction of the product with cysteine. This can sometimes be a problem since if the change in λmax is too great, the chromophore may no longer absorb light in the UVA or UVB wavelength range.

An example of this change is 4-aminobenzophenone which has a λmax of 318 nm which is in the UVB range. When the amino group is replaced by a maleamic acid group, the λmax of the chromophore shifts to 306 nm which is still within the UVB range but when the amino group is replaced by a maleimide residue, the λmax falls to 258 nm. This is outside the range of UVB although there is a restoration of UVB activity when the maleimide is reacted with cysteine as it would be when applied to the skin (λmax=293 nm). The changes are easily rationalised on the basis of conjugative effects but the effects of attaching Michael acceptors to the various chromophores which may be used cannot always easily be predicted. This problem can be overcome to a large extent simply by separating the chromophore from the Michael acceptor using a spacer. Particularly useful compounds therefore include those in which the group R is $C_1$–$C_8$ alkyl-YZ, $C_2$–$C_8$ alkenyl-YZ or $C_2$–$C_8$ alkynyl-YZR and especially those in which Y is O. Compounds in which a hexyloxy linker is used (that is, R is $(CH_2)_6OZ$) are especially preferred.

Examples of compounds of general formula I with a spacer between the Michael acceptor and the chromophore include the following:
N-[6-(4-benzoylphenoxy)hexyl]-maleamic acid;
N-[6-(4-benzoyl-3-hydroxy-phenoxy)-hexyl]-maleamic acid;
N-{6-[4-(2',4'-dihydroxybenzoyl)-3-hydroxy-phenoxyl]-hexyl}-maleamic acid;
N-[6-(4-benzoylphenoxy)hexyl]-maleimide;
N-[6-(4-benzoyl-3-hydroxy-phenoxy)-hexyl]-maleimide;
N-{6-[4'-(2',4'-dihydroxybenzoyl)-3-hydroxy-phenoxy]-hexyl}-maleimide;
N-{6-{[4'-(2"-ethylhexyloxy)-carbonyl-(Z)-ethenyl]-phenoxy}-hexyl}-maleamic acid;
N-{6-{[4'-(2"-ethylhexyloxy)-carbonyl-(Z)-ethenyl]-phenoxy}-hexyl}-maleimide;
N-{6-{[4'-(2"-ethylhexyloxy)-carbonyl-(E)-ethenyl]-phenoxy}-hexyl}-maleamic acid;
N-{6-{[(4'-(2"-ethylhexyloxy)-carbonyl-(E)-ethenyl]-phenoxy}-hexyl}-maleimide;
N-{6-[(4'-ethoxycarbonyl-(Z)-ethenyl)-phenoxy]-hexyl}-maleamic acid;
N-{6-[(4'-ethoxycarbonyl-(Z)-ethenyl)-phenoxy]-hexyl}-maleimide;
N-{6-[(4'-ethoxycarbonyl-(E)-ethenyl)-phenoxy]-hexyl}-maleamic acid;
N-{6-[(4'-ethoxycarbonyl-(E)-ethenyl)-phenoxy]-hexyl}-maleimide;
[4-(2',2'-dimethylethyl)-benzoyl]-[4-(ethenedioic acid monoamide-N-6-hexyloxy)-benzoyl]-methane;
[4-(2',2'-dimethylethyl)-benzoyl]-[4-(6-maleimidohexyloxy)-benzoyl]-methane.

The preferred compounds according to the present invention are, unlike many conventional sunscreens, not irritating to the skin and they will therefore be particularly welcome to the large section of the population who have sensitive skin and are therefore not able to use conventional sunscreens without a considerable degree of discomfort. In addition, on testing for mutagenicity it was surprisingly found that, unlike many known N-alkylmaleimides the compounds of the present invention do not seem to be mutagenic and they also have very low toxicity.

Compounds of general formula I in which X is a maleamic acid residue:

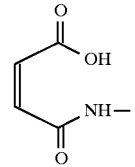

can be prepared by reaction of maleic anhydride with a compound of general formula II or III.

$$RNH_2 \qquad \qquad II$$

$$RNH_3^+ \qquad \qquad III$$

wherein R is as defined in general formula I in an inert solvent such as dichloromethane and in the presence of a tertiary amine such as triethylamine.

Compounds of general formula I in which X is a maleimide residue:

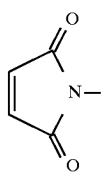

can be prepared from the corresponding maleamic acid compound of general formula I by reaction with a dehydrating agent such as acetic acid in sodium acetate.

Compounds of general formulae II and III can both be prepared from a compound of general formula IV

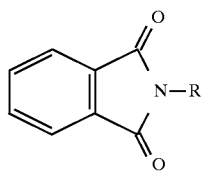

IV wherein R is as defined in general formula I.

In order to obtain a compound of general formula II, the compound of formula IV can be treated with hydrazine whilst, if a compound of general formula III is required, the phthalimide residue can be cleaved in the presence of acid.

Whether the compound of formula I is synthesised via a compound of formula II or formula III will depend upon the nature of the group R. If it is stable in acid but unstable in alkali, then the compound of formula IV will be converted with acid to a compound of formula III whereas if the group R is unstable in acid, the route via a compound of formula II will be used.

A compound of general formula IV can be prepared from a compound of general formula V:

R—Br    V wherein R is as defined in general formula I by reaction with:

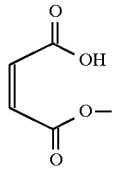

(potassium phthalimide) in a polar solvent such as dimethylformamide (DMF). This route for the conversion of compounds of general formula V to compounds of general formula II is known as the Gabriel synthesis and preferred reaction times and conditions are familiar to those skilled in the art. The Gabriel Synthesis is particularly useful when R is a benzophenone or similar derivative.

An alternative method for the preparation of a compound of general formula III is by reaction of a compound of general formula VI:

R—N(Me$_3$Si)$_2$    VI wherein R is as defined in general formula I. This reaction is carried out in the presence of aqueous acid and is useful when the group R is one which is susceptible to nucleophilic attack in a site other than the one to be coupled to the Michael acceptor. Compounds of general formula VI can be prepared from compounds of general formula V by reaction with

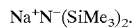

Na$^+$N$^-$(SiMe$_3$)$_2$.

Compounds of general formula V are well known in the art and/or can be prepared by methods known to those skilled in the art.

A third way of preparing compounds of general formula III is by reaction of a compound of general formula VII

R—NHCOO$^t$Bu    VII wherein R is as defined in general formula I, with trifluoroacetic acid to remove the t-butyloxycarbonyl (Boc) protecting group.

Protected amines of general formula VII can be produced from amines similar to those of general formula II. This route is often used when R is a reactive group such as a cinnamic acid derivative. For example, an aryl group can be introduced into a protected amine to give a compound of general formula VII, following which the protecting group can be removed to give a compound of general formula III.

Compounds of general formula I in which X is a maleic acid ester residue:

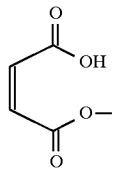

can be prepared by reaction of a compound of general formula VIII:

R—OH    VIII wherein R is as defined in general formula I with maleic anhydride in an acid catalysed esterification reaction.

Alcohol derivatives of general formula VIII are well known or can be prepared by methods known to those skilled in the art, for example from bromides of general formula V.

Compounds of general formula I in which X is a quinone derivative:

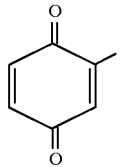

and R is a group Z can be prepared by the reaction of quinone with a compound of general formula IX:

ArN$_2^+$    IX under the conditions described in Org. Synth. Coll. Vol. 4, 15 (1963). For compounds of general formula I in which X is a quinone and R is a substituted Z group such as Z—O (CH$_2$)$_n$, a suitable synthetic route is the reaction of a compound of general formula X:

Z—O(CH$_2$)$_n$CO$_2$H    X wherein Z is as defined in general formula I with quinone under the conditions described in Org. Synth., Coll. Vol. 6, 890 (1988).

Compounds of general formulae IX and X are known in the art or may be prepared by methods familiar to those skilled in the art.

Compounds of general formula I in which X is an acrylic acid residue:

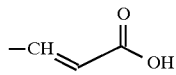

may be prepared by heating a compound of general formula XI:

R—CH=C(CO$_2$Et)$_2$   XI in aqueous acid.

A compound of general formula XI may be obtained by reaction of a compound of general formula XII:

RCHO   XII with diethyl propanedioic ester [(EtO$_2$C)$_2$CH$_2$] in the presence of pyrimidine.

Compounds of general formulae XII are known in the art and may be prepared by methods known to those skilled in the art.

An alternative method for the synthesis of a compound of general formula I in which X is an acrylic acid residue is via the Perkin reaction. In this method, a compound of general formula XIII:

RCHO   XIII is reacted with acetic anhydride in the presence of sodium acetate. This is a particularly suitable method when R is an aryl group.

Again, aldehydes of general formula XIII are well known in the art.

The processes for preparing the compounds of general formula I form a part of the present invention and therefore in another aspect of the invention there is provided a process for the preparation of a compound of general formula I, the process comprising:

a. when X is a maleamic acid residue, reacting maleic anhydride with a compound of general formula II or general formula III in an inert solvent such as dichloromethane, optionally in the presence of an amine such as triethylamine;

b. when X is a maleimide residue, reacting the compound of general formula I produced in step (a) with a dehydrating agent such as acetic acid and sodium acetate;

c. when X is a maleic acid ester residue, reacting a compound of general formula VIII with maleic anhydride;

d. when X is a quinone residue, reacting quinone with a compound of general formula IX or general formula X; or e. when X is an acrylic acid residue, heating a compound of general formula XI in aqueous acid conditions or reacting an aldehyde of general formula XIII with acetic anhydride;

wherein general formulae II, III, VIII, IX, X, XI and XIII are as defined above.

The compounds of the present invention may be formulated as creams, lotions or oils for topical administration to the skin. Conventional dermatologically acceptable excipients are well known to those skilled in the art and include fats, paraffin, emollients etc.

Thus, in a further aspect of the invention, there is provided a sunscreen formulation comprising a compound of the present invention together with a dermatologically acceptable excipient or carrier.

In a further aspect of the invention, there is provided a process for screening the skin from the sun, comprising applying to the skin a sunscreen compound as described above.

Because of their ability to screen the skin from the sun for prolonged periods of time, the compounds of the invention will be of assistance in preventing dermatological conditions arising from exposure to sunlight, for example erythema, premature aging, skin cancers and other conditions caused by prolonged exposure to sunlight.

Therefore, in a further aspect of the invention there is provided a compound of the invention for use in the prevention of dermatological conditions related to exposure to sunlight.

The invention also comprises a method for the prevention of a dermatological condition arising from exposure to sunlight, the method comprising administering to a patient an effective amount of a compound as described above.

In an additional aspect of the invention there is provided the use of a compound as described above in the preparation of an agent for the prevention of dermatological conditions arising from exposure to sunlight.

The invention will now be further illustrated by reference to the following examples and to the drawings in which:

FIG. 1 is a plot showing the change in the absorption spectrum of hair keratin after reaction with N-phenylmaleimide; and FIG. 2 is a plot showing the change in the absorption spectrum of horn-hoof keratin after reaction with N-phenylmaleimide.

EXAMPLE 1

N-(4-carboxyphenyl)maleamic Acid

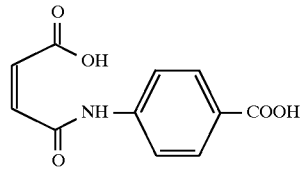

4-Aminobenzoic acid (17.24 g, 0.1257 mol) was added to a stirred solution of maleic anhydride (12.33 g, 0.1257 mol) in propanone (300 ml). Stirring was continued at room temperature for 3 hours. The product, which separated as a yellow solid, was collected by suction filtration and dried on the filter: mp 217°–219° C. (Ref: K C Liu, *J. Chin. Chem. Soc.*, 1973, 20, 163).

EXAMPLE 2

N-(4-carboxyphenyl)maleimide

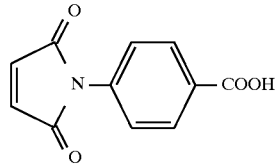

The product from Example 1 (20.00 g, 0.0852 mol) was added to a stirred solution of anhydrous sodium ethanoate (4.00 g) in ethanoic anhydride (200 ml) and the mixture heated with stirring at 90°–95° C. until dissolution was complete. The solution was allowed to cool to room temperature, with stirring and, after a further 2 hours, poured slowly into an ice-5% aqueous sodium bicarbonate solution (2 L). The precipitate was filtered at the pump, washed with diethyl ether (3×30 ml) and air dried. Purification of the product by flash chromatography using chloroform as eluent yielded the maleamic acid (Ref: K C Liu, *J. Chin. Chem. Soc.*, 1973, 20, 163).

EXAMPLE 3

N-(4-benzoylphenyl)maleamic Acid

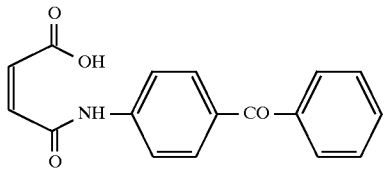

4-Aminobenzophenone (10.00 g, 0.0507 mol) was added to a stirred solution of maleic anhydride (4.98 g, 0.0508 mol) in dichloromethane (200 ml). After 10 minutes of stirring at room temperature, yellow precipitate was formed. Stirring was continued for a further 3 hours, following which the solid was collected, washed with dichloromethane (3×30 ml) and diethyl ether (2×30 ml) and finally air dried to yield the maleanmic acid. (Found: C, 68.74; H, 4.57; N, 4.41%. $C_{17}H_{13}NO_4$ requires C, 69.15; H, 4.44; N, 4.74%). H.p.l.c (Kromazil $C_{18}$, 49.95% MeOH, 49.95% $H_2O$, 0.1% $CF_3CO_2H$): 99.7% $\lambda_{max}$ 306 nm; ε 20560. $^1$H-n.m.r (DMSO): δ 10.62 (1H, s, NH); 7.8–7.5 (9H, m, phenyl); 6.45 (1H, d; CH=CH); 6.31 (1M, d, CH=CH); 3.38 (1H, S, $CO_2H$).

EXAMPLE 4

N-(4-benzoylphenyl)maleimide

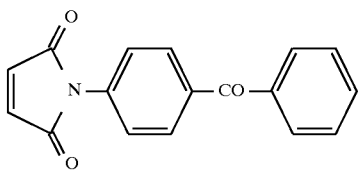

The method of Example 2 was employed, but, in place of the product of Example 1 the maleamic acid from Example 3 (15.0 g, 0.0508 mol) and anhydrous sodium ethanoate (3.00 g) in ethanoic anhydride (150 ml) were used. The maleimide was obtained. $^1$H-n.m.r (DMSO): δ 7.91 (4H, m, N-Ph); 7.52 (5H, m, Ph); 6.89 (2H, s, CH=CH), H.p.l.c. 100%.

EXAMPLE 5

N-[4-(2-carboxy-(E)-ethenyl)phenyl]maleamic Acid

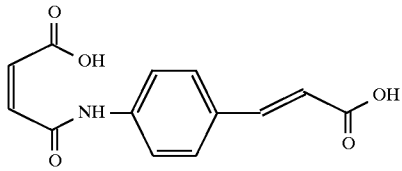

The method of Example 1 was employed using 4-aminocinnamic acid hydrochloride (10.0 g, 0.0501 mol) and maleic anhydride (5.00 g, 0.0509 mol). Triethylamine (7.00 ml, 0.0502 mol) in dichloromethane (100 ml) was added to generate the free amine. The yellow maleamic acid was obtained. H.p.l.c. 100%. $^1$H-n.m.r. (DMSO): δ 10.51 (1H, s, NH); 7.65 (4H, bs, ar H's); 7.55 (1H, d, pH-CH); 6.44 (2H, t, $HO_2C$ CH=CH; CO, PhCH=CH); 6.30 (1H, d, $HO_2C$ CH=CH CO).

EXAMPLE 6

N-[4-(2-carboxy-(E)-ethenyl)phenyl]maleimide

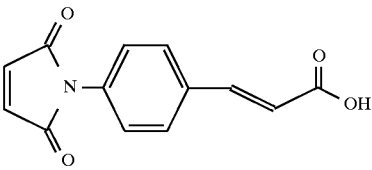

This preparation was carried out as for the method described for Example 2 using the product from Example 5 (10.0 g, 0.038 mol). Purification was carried out by flash column chromatography with 10% methanol—90% chloroform as eluent. The maleimide was obtained. H.p.l.c. 99.81%. $^1$H-n.m.r. (CDCl$_3$): δ 7.80 (2H, d, 2, 6H on phenyl); 7.61 (1H, d, CH=CH $CO_2H$); 7.38 (2H, d, 3,5-H on phenyl); 7.20 (2H, s, CH=CH); 6.57 (1H, d, CH=CHCO$_2$H).

EXAMPLE 7

N-(4-methoxycarbonylphenyl)maleamic Acid

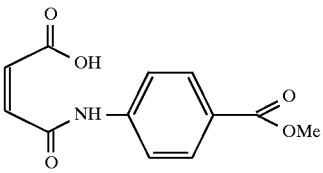

The method described in Example 5 was employed using methyl 4-aminobenzoate hydrochloride (10.0 g, 0.053 mol). the maleamic acid was obtained. (Found C, 57.60; H, 4.55; N, 5.52%. $C_{12}H_{11}NO_5$ requires C, 57.83; H, 4.45; N, 5.62%). $^1$H-n.m.r. (DMSO) δ 10.65 (1H, s, NH); 7.91 (2H, d, 2,6-H of phenyl); 7.75 (2H, d, 3,5-H of phenyl); 6.51 (1H, d, CH=CH); 6.32 (1H, d, CH=CH); 3.82 (3H, s, $CH_3$). H.p.l.c. 99.31%. $\lambda_{max}$ 294 nm: ε 16013.

EXAMPLE 8

N-(4-methoxycarbonylphenyl)maleimide

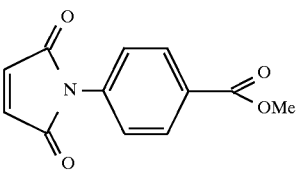

The method described in Example 2 was employed using the product from Example 7 (10.0 g, 0.04 mol). The maleimide was obtained as a golden yellow solid. (Found C, 61.77; H, 4.06; N, 5.89%. $C_{12}H_9NO_4$ 0.1 $H_2O$ requires C, 61.86; H, 3.98; N, 6.01%). H.p.l.c. 99.73%. $^1$H-n.m.r.

(CDCl₃): 8.06 (2H, d, 2,6-H on phenyl); 7.42 (2H, d, 3,5-H on phenyl); 6.81 (2H, s, CH═CH) 3.85 (3H, s, CH₃). $\lambda_{max}$ 245 nm, $\epsilon$ 15844.

EXAMPLE 9

N-(4-n-butyloxycarbonylphenyl)maleamic Acid

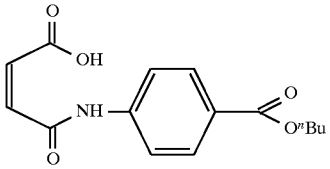

The maleamic acid was prepared using the method described in Example 7 but butyl ester (12.20 g, 0.053 mol) was used in place of the methyl ester. The product was obtained as an off-white solid. (Found C, 61.71; H, 5.74; N, 4.67%. $C_{15}H_{17}NO_5$ requires C, 61.85; H, 5.88; N, 4.81%). H.p.l.c. 99.90%. ¹H-n.m.r. (DMSO): δ 10.61 (1H, s, NH); 7.85 (2H, d, 2,6-H of phenyl); 7.73 (2H, d, 3,5H of phenyl); 6.45 (1H, d, CH═CH); 6.32 (1H, d, CH═CH); 4.21 (2H, m, CH₂); 1.62 (2H, m, CH₂). $\lambda_{max}$ 294 nm, $\epsilon$ 15806.

EXAMPLE 10

N-(4-n-butyloxycarbonylphenyl)maleimide

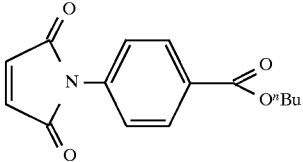

The maleimide was prepared as in Example 8 using the product from Example 8 (10.0 g, 0.034 mol) in place of the methyl ester. The product was obtained as an off-white solid. (Found C, 65.70; H, 5.69; N, 5.05%. $C_{15}H_{15}NO_4$ requires C, 65.93; H, 5.53; N, 5.13%). H.p.l.c. 99.89%. ¹H-n.m.r. (CDCl₃): 8.11 (2H, d, 2,6H of phenyl); 7.46 (2H, d, 3,5H of phenyl); 6.83 (2H, s, CH═CH); 4.29 (2H, t, CH₂CH₂O); 1.71 (2H, m, CH₂ CH₂O); 1.44 (3H, m, CH₃, CH₂); 0.94 (3H, t, CH₃). $\lambda_{max}$ 245, $\epsilon$ 15563.

EXAMPLE 11

N-[6-(4-benzoylphenoxy)-hexyl]-maleamic Acid

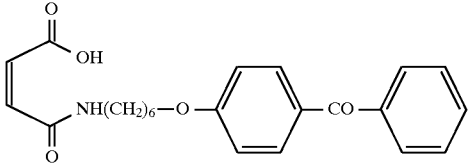

The steps for the preparation of this compound were as follows.
A. Preparation of 4-(6-bromohexyloxy)-benzophenone To a solution of sodium ethoxide, prepared by dissolving sodium (1.30 g, 0.055 mol) in absolute ethanol (150 ml), was slowly added 1-benzoyl-4-hydroxy-benzene (10 g, 0.05 mol). The resulting solution was added dropwise to a stirred solution of 1,6-dibromohexane (36.6 g, 0.15 mol) in ethanol heated under reflux. Stirring and heating were continued for 8 hours during which time sodium bromide was formed as a crystalline precipitate. Removal of the sodium bromide by filtration and evaporation of the filtrate in vacuo gave a white solid which was washed with ethanol (30 ml). The ethanol washings were concentrated to 10 ml and the product isolated by flash column chromatography using chloroform as eluent to yield the bromohexyl derivative as white crystals. (Found: C, 63.12; H, 6.18%. $C_{19}H_{21}BrO_2$ requires C, 63.17; H, 5.86%). FAB ms 362 and 360 (MH⁺). ¹H-n.m.r. (DMSO) δ 7.8–6.9 (9H, m, aromatic); 4.02 (2H, t, CH₂); 3.41 (2H, m, CH₂); 1.99–1.80 (2×CH₂); 1.50 (2×CH₂).

B. Preparation of N-[6-(4-benzoylphenoxy)-hexyl]-phthalimide

Potassium phthalimide (5.75 g, 0.031 mol) was added to a solution of the product from A (10.2 g, 0.028 mol) in dimethylformamide (250 ml). The reaction mixture was heated at 60° C. for 16 hours. Chloroform (300 ml) was added and the mixture poured into distilled water (1.4 L). The chloroform layer was separated and the aqueous layer extracted with chloroform (2×75 ml). The combined chloroform layers were washed successively with 0.2M sodium hydroxide (150 ml) and water (150 ml), dried over anhydrous magnesium sulphate and evaporated to yield a gum which produced white crystals of the desired phthalimide derivative and its hydrate on trituration with diethyl ether. (Found: C, 74.37; H, 5.96; N, 3.24%. $C_{27}H_{25}NO_4$ 0.5 H₂O requires C, 74.29; H, 6.00; N, 3.21%). FAB ms 428 (MH⁺). ¹H-n.m.r. (CDCl₃) δ 7.8–7.6 (6H, m, aromatic); 7.5 (2H, m, aromatic); 7.4 (3H, m, aromatic); 6.7 (2H, m, aromatic); 4.0 (2H, t, CH₂N); 3.7 (2H, t, CH₂O); 1.8–1.4 (8H, m, 4×CH₂). ¹³C-n.m.r. (CDCl₃) δ 168.49 (C═O); 168.38 (CON); 162.68–113.91 (aromatic); 67.96 (CH₂); 37.79 (CH₂); 28.86 (CH₂); 28.44 (CH₂); 26.48 (CH₂); 25.55 (CH₂).

C. 4-(6-Axmoniohexyloxy)-benzophenone Chloride

The product from B (above) (9.00 g, 0.021 mol) was added to a mixture of ethanoic acid (200 ml) and concentrated hydrochloric acid (200 ml) and the mixture heated under reflux for 36 hours with further additions of 1:1 ethanoic acid and hydrochloric acid (100 ml) after 4 and 24 hours. The resulting solution was treated with charcoal, filtered and the filtrate washed into an evaporating flask with chloroform. Evaporation yielded the hydrochloride as an off-white solid on trituration with diethyl ether. (Found: C, 60.33; H, 6.67; N, 3.74%. $C_{19}H_{24}NClO_2$ 0.45 CHCl₃ requires C, 60.28; H, 6.36; N, 3.61%). ¹H-n.m.r. (CDCl₃) δ 7.9 (3H, bs, N⁺H₃); 7.6–7.5 (9H, m, aromatic); 4.2 (2H, t, CH₂N); 2.8 (2H, t, CH₂O); 1.8–1.4 (4H, m, 2×CH₂); 1.4–1.2 (4H, m, 2×CH₂).

D. 1-Benzoyl-4-(ethendioic Acid Monoamide-N-hexyl-6-oxy)-benzene (Example 11)

The product from C (above) (5.00 g, 0.015 mol) was treated as for Example 5 using maleamic acid (1.47 g, 0.015 mol). Column chromatography on silica gel with 10% MeOH, 90% chloroform yield the pure title compound as its hydrate mp 114—6° C. (Found: C, 68.97; H, 6.31; N, 3.39%. $C_{23}H_{25}NO_5$ 0.4 H₂O requires C, 68.61; H, 6.46; N, 3.48%) FAB ms 396 (MH⁺). ¹H-n.m.r. (CDCl₃) δ 8.2 (1H, bs, NH), 7.8–7.4 (7H, m, aromatic), 6.9 (2H, d, aromatic), 6.4 (1H, d, CH═C), 6.2 (1H, d, CH═C), 3.8 (2H, m, CH₂N), 3.3 (2H, m, CH₂O), 1.8–1.3 (8H, m, 4×CH₂). $\lambda_{max}$ (CH₂Cl₂) 285 nm, $\epsilon$ 16047. H.p.l.c. 99.7%.

EXAMPLE 12

N-[6-(4-benzoylphenoxy)-hexyl]-maleimide

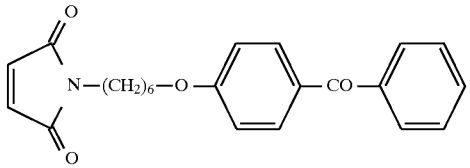

The compound can be prepared from N-[6-(4-benzoylphenoxy)-hexyl]-maleamic acid from Example 11 by reacting with acetic acid and sodium acetate according to the method described in Example 2. The desired maleimide was isolated as its monohydrate by flash column chromatography. Mp 84—6° C. (Found: C, 72.78; H, 6.28; N, 3.58%. $C_{23}H_{23}NO_3$, $H_2O$ requires C, 73.19; H, 6.65; N, 3.69%). H.p.l.c. 100%. FAB ms 378 (MH$^+$). $^1$H-n.m.r. (CDCl$_3$) δ 6.9 (2H, m, aromatic), 6.6 (2H, d, CH=CH), 3.9 (2H, m, CH$_2$), 3.5 (2H, m, CH$_2$), 1.8 (2H, m, CH$_2$), 1.6 (2H, m, CH$_2$), 1.5 (2H, m, CH$_2$), 1.3 (2H, m, CH$_2$). $\lambda_{max}$ (CH$_2$Cl$_2$) 286 nm, ε 16590.

EXAMPLE 13

N-[6-(4-benzoyl-3-hydroxy-phenoxy)-hexyl]-maleamic Acid

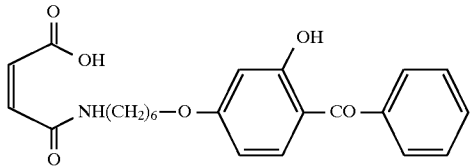

This compound can be prepared according to the following method.

A. 4-(6-Bromohexyloxy)-2-hydroxy-benzophenone

The preparative method employed was analogous to that in Example 10 A using 2,4-dihydroxybenzophenone (20.00 g, 0.088 mol) in place of benzophenone. The product was isolated as off-white crystals and was used without further purification in B (below).

B. N-[6-(4-benzoyl-3-hydroxy-phenoxy)-hexyl]-phthalimide

The product from A was treated in an analogous manner to that described in Example 10 B (above), and the product was isolated in 42.5% yield by column chromatography (SiO$_2$ gel—10% ethyl ethanoate in hexane).

C. 4-(6-Ammoniohexyloxy)-2-hydroxy-benzophenone Hydrochloride

The product from B (3.00 g, 0.00676 mol) was treated as for Example 10 C (above). The product hydrochloride was obtained as a tan-coloured solid.

D. N-[6-(4-benzoyl-3-hydroxy-phenoxy)-hexyl]-maleamic Acid

The product from C (1.00 g, 0.00286 mol) was reacted with maleic anhydride as described in Example 13 D and the pure title compound as its monohydrate was isolated as a tan-coloured solid. (Found: C, 64.66; H, 6.04; N, 3.34%. $C_{23}H_{25}NO_6$ $H_2O$ requires C, 64.32; H, 6.34; N, 3.26) H.p.l.c. 99.3%. FAB ms 412 (MH$^+$). $^1$H-n.m.r. (CDCl$_3$) δ 12.8 (1H, bs, NH), 7.8–7.2 (8H, m, aromatic), 6.5–6.1 (3H, d+s, CH=CH, OH), 4.1 (2H, m, CH$_2$), 3.3 (2H, m, CH$_2$), 1.9–1.2 (9H, m, 4×CH$_2$+OH).

EXAMPLE 14

N-[6-(4-benzoyl-3-hydroxyphenoxy)-hexyl]-maleimide

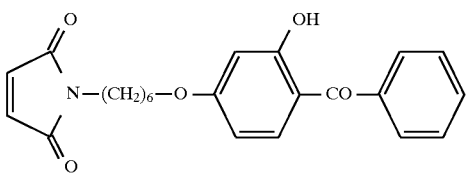

This compound was prepared from the product of Example 13 using the method of Example 2.

In order to demonstrate that the compounds of the invention are capable of binding to keratin, the following experiments were carried out.

EXAMPLE 15

N-{6-[4-(2',4'-Dihydroxybenzoyl)-3-hydroxyphenoxy]hexyl}-maleamic Acid

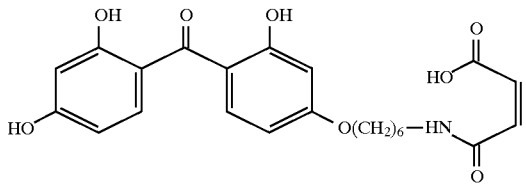

A. 4-[6-(N-t-Butyloxycarbonyl)aminohexyloxy]-2,2',4'-trihydroxybenzophenone

Sodium (3.48 g, 152 mmole) was dissolved in absolute ethanol (500 ml). The mixture was purged with nitrogen and 2,2',4,4'-tetrahydroxybenzophenone (37.5 g, 152 mmole) added. Methane sulphonic acid 6-(N-t-butyloxycarbonyl) aminohexyl ester (15 g, 50 mmole) was added. The mixture was refluxed for 27 h, then filtered. The filtrate was concentrated to dryness and redissolved in chloroform. An oil which solidified, separated and was removed by filtration. The filtrate was concentrated to dryness and the process repeated twice. The final filtrate was concentrated to dryness and chromatographed over silica gel using chloroform/methanol 9:1 to give the product (20.14 g, 89%) NMR (d$^6$-DMSO): δ 11.48 (1H, s, OH), 11.1 (1H, s, OH), 10.3 (1H, s, OH), 7.25–7.15 (2H, m, ArCH), 6.44–6.48 (2H, m, ArCH), 6.29–6.36 (2H, m, ArCH), 3.93–4.0 (2H, m, OCH$_2$), 2.83–2.89 (2H, m, NCH$_2$), 1.34–1.69 (17H, m, t-butyl, 4×CH$_2$). m/e: 446 (M$^+$+1; 6%), 346 (30%), 137 (100%).

B. 4-(6-Ammoniohexyloxy)-4',2,2'-trihydroxybenzophenone Chloride 4-(6-(N-t-Butyloxycarbonyl)aminohexyloxy)-2,2',4'-trihydroxybenzophenone (18 g) was dissolved in methanol (250 ml) and cooled on ice. Concentrated hydrochloric acid (50 ml) was added dropwise. After 15 minutes, concentrated hydrochloric acid (25 ml) was added and the mixture stirred at room temperature overnight. The solvent was removed and the residue crystallised from ethanol/ether to yield the title compound (7.9 g, 56.6%). NMR(d$^6$-DMSO): δ 7.15–7.26 (2H, m, ArCH), 6.44–6.49 (2H, m, ArCH), 6.28–6.33 (2H, m, ArCH), 3.95–4.03 (2H, m, OCH$_2$), 2.71–2.79 (2H, m, NCH$_2$), 1.33–1.73 (8H, m, 4×CH$_2$). m/e 346 (M$^+$+1; 86% 253 (100%).

C. N-{6-[4-(2',4'-Dihydroxybenzoyl)-3-hydroxyphenoxy]hexyl}-maleamic Acid 4-(6-Aminohexyloxy)4'2,2'-trihydroxybenzophenone (1 g, 2.6 mmole) and maleic anhydride (255 mg, 2.6 mmole) were suspended in methylene chloride (50 ml) and triethylamine (265 mg, 2.6 mmole) added. The mixture was stirred at room temperature for 2.5 days. Triethylamine (265 mg, 2.6 mmole) was added and the mixture stirred for a further 18 h. It was filtered, the filtrate concentrated and the residue redissolved in chloroform (50 ml). This solution was treated with aqueous HCl (25 ml, 1.2M) whereupon a precipitate formed. This was filtered off and dried (440 mg, 38%) NMR ($d^6$-DMSO) δ 11.49 (1H, s, OH), 11.14 (1H, s, OH), 10.35 (1H, s, OH), 7.17–7.24 (2H, m, ArCH), 6.21–6.48 (6H, m, 4×ArCH, 2×CH of acid), 3.97–4.03 (2H, t, $CH_2O$), 3.15–3.20 (2H, m, $NCH_2$), 1.69–1.72 (2H, m, $CH_2$), 1.31–1.51 (6H, m, $3×CH_2$) m/e: 444 ($M^+$+1, 40%), 176 (100%).

EXAMPLE 16

N-{6-[(4'-Ethoxycarbonyl-(Z)-ethenyl)phenoxy]hexyl}-maleamic Acid

A. Ethyl 4-[6-(N-t-butyloxycarbonyl)-aminohexyloxy]phenylethenoate

Ethyl 4-hydroxycinnamate (2.0 g) was dissolved in dry THF (20 ml), potassium hydroxide (1.17 g) was added and the mixture stirred for 1 hour. A solution of 6-(N-t-butyloxycarbonyl)amino-hexanol methanesulphonate (3.07 g) in THF (12 ml) was added dropwise during 30 min and the mixture stirred for 3 h in a vessel protected by a calcium chloride guard tube. The solution was heated under reflux for 1.25 h, cooled, and the gel-like precipitate removed by filtration. Concentration of the filtrate gave the title compound as a pale yellow oil which crystallised on standing (4.47 g, 110% as solvate) $^1$H nmr ($CDCl_3$): δ 7.62(1H, d, ArCH=CH), 7.44(2H, d, Ar-m-H) 6.86(2H,d,Ar-o-H), 6.28 (1H, d, =CHCO), 4.5(1H, br, NH), 4.23(2H, q, $CH_2CH_3$), 3.9(2H, t, $CH_2O$), 3.7(2H, t, $CH_2CH_2O$), 3.1(4H, m, $2×CH_2$), 1.7–1.9(4H, m, $2×CH_2$), 1.42(9H, s, $(CH_3)_3C$), 1.27(3H, t, $CH_3$).

B. Ethyl 6-ammoniohexyloxy)phenyl Ethenoate Chloride

The product from A (2.0 g) was dissolved in ethanol (27.5 ml) and the solution cooled to 0° C. Conc. hydrochloric acid (5.5 ml) was added dropwise over 10 min and the solution allowed to warm to room temperature with stirring. A further addition of conc. hydrochloric acid (2.7 ml) was made after 1 h and stirring continued for a further 23 hours. Evaporation in vacuo yielded a white crystalline solid which was dried by co-evaporation with ethanol (15 ml). Recrystallisation from ethanol gave the 40 title compound as white platelets (1.4 g, 84%). M.s(FB)$M^+$292.

C. N-{6-[(4'-Ethoxycarbonyl-(Z)-ethenyl)phenoxy]hexyl}-maleamic Acid

Maleic anhydride (1.5 g) was dissolved in acetonitrile (15 ml) and a suspension of the product from B above (1 g) in acetonitrile (15 ml) was added. The suspension was stirred and triethylamine was added dropwise. The resulting clear solution was stirred for 1 h, 1.2M hydrochloric acid (25 ml) was added and stirring continued for a further 1.5 h. The precipitate which formed was collected, washed with 1.2M hydrochloric acid (3 ml) and dried by suction on the filter to yield the title compound as a white powder (0.33 g, 28%) mp 135.5°–136.5° C. Hplc (80:20 MeOH:$H_2O$), m.s (FAB) $MH^+$390. NMR ($d^6$-DMSO) δ 9.13–9.14 (1H, bm, NH), 7.58–7.67 (3H, m, 2×ArCH, alkenyl CH), 6.94–6.97 (2H, d, 2×ArCH), 6.23–6.49 (3H, m, alkenyl CH), 4.14–4.20 (2H, q, $CH_3CH_2$), 3.99–4.03 (2H, t, $CH_2CH_2O$), 3.16–3.22 (2H, q, $CH_2N$), 1.70–1.75 (2H, m, $CH_2$), 1.32–1.54 (6H, m, $3×CH_2$), 1.23–1.27 (3H, t, $CH_3$).

EXAMPLE 17

Reaction of Maleimide Derivatives with L-cysteine Ethyl Ester

In order to underpin the principle of reaction of maleimido derivatives with the cysteine thiol groups, two model reactions were studied. Thus the reactions between L-cysteine ethyl ester and N-phenylmaleimide and N-(4-benzoylphenyl)maleimide were carried out. In each case, the reaction produced the diastereoisomeric product mixtures in reasonable yields at room temperature. All starting maleimides had reacted within 30 minutes (tlc). The two products were isolated and characterised.

The mildness and rapidity of these reactions indicate that the maleimido groups confer the ability for reaction with the nucleophilic groups of keratin.

EXAMPLE 18

Substantivity Tests with Keratin

In order to demonstrate that the maleimides are capable of binding to keratin, the following tests were carried out using N-phenylmaleimide as a model compound.

Initial tests were conducted with human hair specially cleaned and prepared to provide as near to a standard substrate as possible. The method adopted utilised the reduction in ultra-violet absorptivity in the supernatant solution in contact with hair when the compound under test was absorbed into the hair surface. Standard and control solutions were employed. It was found that the standardisation of hair, coupled with the difficulty of handling a readily static-charged material, was impossible to achieve. Nevertheless, all results showed that substantivity was a feature of the N-phenylmaleimide used as a model compound, considerable reduction in absorptivity being observed. Similar tests with hair have been quoted in the patent literature as evidence, and as a standard test, for substantivity of sunscreens and other cosmetics.

Keratin prepared from the horns and hooves of various animals is commercially available, and this was used in a similar way to the hair (above). The keratin was finely powdered and stirred with a solution of the maleimido compound and its substantivity estimated by uv absorptivity measurements. The results were found to parallel those obtained with hair (Table 2 and FIGS. 3 and 4).

Results of substantivity tests on N-phenylmaleimide with hair and horn-proof keratin

| Wt of hair (g) | Wt maleimide added (g) | Wt maleimide absorbed (g) (uv assay) | Substantivity (%) |
|---|---|---|---|
| 1.0000 | 0.4520 | 0.0837 | 18.5 |
| 1.0000 | 0.4670 | 0.1421 | 30.4 |
|  |  | Average: 0.1129 g | 24.5% |

| Wt of horn hoof keratin (g) | Wt maleimide added (g) | Wt maleimide absorbed (g) | Substantivity (%) |
|---|---|---|---|
| 1.0000 | 0.4360 | 0.0968 | 22.2 |
| 1.0000 | 0.4741 | 0.1001 | 21.1 |
|  |  | Average: 0.0985 g | 21.7% |

The results indicate that the incorporation of a maleimido residue resulted in chemico-physical interactions with the keratin component of hair and the hard tissues of the epidermis. The method is extensively used to establish substantivity and the measurements are an indirect indication of persistence of the molecules on the hair or skin.

EXAMPLE 19

Biological Results: Mutagenicity and Toxicity Studies

Among the important criteria for topically applied sunscreens, safety in use has the highest priority. It was thus necessary to investigate the mutagenicity of the maleimide and maleamic acid derivatives of sunscreens. Six compounds of the present invention were chosen as representative of the main classes of sunscreen and submitted for Ames tests. The results are summarised in Table 2. The tests demonstrated that none of the compounds were mutagenic below toxic levels, with or without the presence of rat liver metabolic activation system S9, that the maleamic acid derivatives showed only slight toxicity and that the maleimides were mildly toxic.

TABLE 2

Toxicity and mutagenicity test results

| EXAMPLE | FORMULA | TOXICITY/μG plate$^{-1}$ | | Mutagenicity |
| --- | --- | --- | --- | --- |
| | | +S9 | −S9 | |
| 3 | CO₂H-CH=CH-C(O)-NH-C₆H₄-CO-C₆H₅ | 2500 | 2500 | Negative |
| 4 | maleimide-N-C₆H₄-CO-C₆H₅ | 100 | 40 | " |
| 1 | CO₂H-CH=CH-C(O)-NH-C₆H₄-CO₂H | 5000 | 5000 | " |
| 2 | maleimide-N-C₆H₄-CO₂H | 500 | 500 | " |
| 5 | CO₂H-CH=CH-C(O)-NH-C₆H₄-CH=CH-CO₂H | 5000 | 5000 | " |
| 6 | maleimide-N-C₆H₄-CH=CH-CO₂H | 200 | 200 | " |
| 11 | CO₂H-CH=CH-C(O)-NH(CH₂)₆O-C₆H₄-CO-C₆H₅ (2) | 2500 | 2500 | " |
| 12 | maleimide-N(CH₂)₆O-C₆H₄-CO-C₆H₅ (3) | 800 | 200 | " |

TABLE 2-continued

Toxicity and mutagenicity test results

| EXAMPLE | FORMULA | TOXICITY/μG plate$^{-1}$ | | Mutagenicity |
|---|---|---|---|---|
| | | +S9 | −S9 | |
| | (structure: maleimide with NEt) | 50 | 25 | slight-not statistically significant |

We claim:

1. A method of protecting a subject against the harmful effects of ultraviolet radiation comprising topically administering a compound comprising a UV chromophore attached to a group which is capable of covalently binding to mammalian skin, wherein the group capable of covalently binding to mammalian skin is a Michael acceptor attached directly or indirectly to the UV chromophore.

2. The method of claim 1 wherein the Michael acceptor is maleic acid, maleamic acid or maleimide, or a derivative of one of these.

3. The method of claim 1 wherein the Michael acceptor is separated from the chromophore by a spacer.

4. The method of claim 1 wherein the compound is of the formula I(a):

$$X\text{—}R \qquad \qquad I(a)$$

wherein

X is a Michael acceptor;

R is Z, $C_1$–$C_8$ alkyl-YZ, $C_2$–$C_8$ alkenyl-YZ or $C_2$–$C_8$ alkynyl-YZ;

Y is O, $NR^4$, $S(O)_n$, C═O or $CH_2$ and n is an integer from 0 to 2;

wherein $R^4$ is H, $C_1$–$C_8$ alkyl or $C_2$–$C_8$ alkenyl; and

Z is a chromophore group.

5. The method of claim 1 wherein the compound is:

N-(4-carboxyphenyl)maleamic acid;

N-(4-carboxyphenyl)maleimide;

N-(4-benzoylphenyl)maleamic acid;

N-[4-2(2-carboxy-(E)-ethenyl)phenyl] maleamic acid;

N-[4-2(2-carboxy-(E)-ethenyl)phenyl] maleimide;

N-[4-2(2-carboxy-(Z)-ethenyl)phenyl] maleamic acid;

N-[4-2(2-carboxy-(Z)-ethenyl)phenyl] maleimide;

N-(4-methoxycarbonylphenyl) maleamic acid;

N-(4-methoxycarbonylphenyl) maleimide;

N-(4-n-butyloxycarbonylphenyl) maleamic acid; or

N-(4-n-butyloxycarbonylphenyl) maleimide.

* * * * *